United States Patent
Henkelmann et al.

[11] Patent Number: 6,153,786
[45] Date of Patent: Nov. 28, 2000

[54] METHOD FOR PRODUCING 2-ALKYNOIC ACID ESTERS

[75] Inventors: Jochem Henkelmann, Mannheim; Thomas Preiss, Ludwigshafen; Arnd Böttcher, Frankenthal; Rolf Gleiter, Heidelberg, all of Germany; Christel de Backer, Muizen, Belgium

[73] Assignee: BASF Aktiengesellschaft, Ludwigshafen, Germany

[21] Appl. No.: 09/402,893

[22] PCT Filed: Apr. 7, 1998

[86] PCT No.: PCT/EP98/02021

§ 371 Date: Oct. 13, 1999

§ 102(e) Date: Oct. 13, 1999

[87] PCT Pub. No.: WO98/46555

PCT Pub. Date: Oct. 22, 1998

[30] Foreign Application Priority Data

Apr. 15, 1997 [DE] Germany .............. 197 15 697

[51] Int. Cl.[7] .................................................. C07C 69/00
[52] U.S. Cl. .............................................................. 560/129
[58] Field of Search ................................................ 560/129

[56] References Cited

FOREIGN PATENT DOCUMENTS 871888  5/1979  Belgium .
56-097250  8/1981  Japan .

OTHER PUBLICATIONS

Yamamoto et al., *J. Am. Chem. Soc.*, 103, 1981, 6133–6136.

*Primary Examiner*—Joseph K. McKane
*Assistant Examiner*—Joseph Murray
*Attorney, Agent, or Firm*—Keil & Weinkauf

[57] ABSTRACT

A process for preparing 2-alkynoic esters of the general formula (I), $$R^1-O-CO-C\equiv C-R^2 \qquad (I)$$

in which $R^1$ and $R^2$ independently are $C_{1-16}$-alkyl, $C_{6-12}$-aryl, $C_{7-12}$-aralkyl or $C_{7-12}$-alkylaryl radicals, and $R^2$ can also be hydrogen, by reacting a chloroformate of the general formula (II), $$R^1-O-CO-Cl \qquad (II)$$

with an alkyne of the general formula (III), $$R^2-C\equiv C-H \qquad (III)$$

is carried out in the presence of a Pt and/or Pd complex which has phosphine ligands and/or phosphite ligands as catalyst.

9 Claims, No Drawings

METHOD FOR PRODUCING 2-ALKYNOIC ACID ESTERS

This application is a 371 of PCT/EP98/02021 filed Apr. 7, 1998.

The invention relates to a process for preparing 2-alkynoic esters and to the use of certain catalysts for their preparation.

2-Alkynoic esters such as propiolic esters are important organic synthons and are used, inter alia, in the drugs sector. They can further be employed as fungicides or bactericides.

Numerous processes for preparing them are known.

JP-A 56 097 250 discloses the preparation of 2-alkynoic esters by reacting phenylacetylene with methanol and carbon monoxide in the presence of an oxidizing agent such as a combination of $PdCl_2$, $CuCl_2$ and alkali metal carboxylate in the presence of a catalyst such as $PdCl_2$, $Pd(NO_3)_2$ or $PdSO_4$.

BE-A 871 888 discloses a process for preparing 2-alkynoic esters in which acetylenic compounds and dialkyl carbonates are reacted in the presence of a strong base. For example, dimethyl carbonate is reacted with 3-methyl-1-butyn-3-ol in the presence of sodium methanolate to give the methyl ester of 4-methyl-4-hydroxypentynoic acid.

Some of the above processes involve elaborate procedures, and they do not always give satisfactory results.

It is an object of the present invention to provide a process for preparing 2-alkynoic esters which leads directly to the required products under very mild conditions and with very high yields.

We have found that this object is achieved by a process for preparing 2-alkynoic esters of the general formula (I),

$$R^1\text{—O—CO—C}\equiv\text{C—}R^2 \quad (I)$$

in which $R^1$ and $R^2$ independently are $C_{1-16}$-alkyl, $C_{6-12}$-aryl, $C_{7-12}$-aralkyl or $C_{7-12}$-alkylaryl radicals, and $R^2$ can also be hydrogen,
by reacting a chloroformate of the general formula (II),

$$R^1\text{—O—CO—Cl} \quad (II)$$

in which $R^1$ has the above meaning,
with an alkyne of the general formula (III),

$$R^2\text{—C}\equiv\text{C—H} \quad (III)$$

in which $R^2$ has the above meaning, in the presence of a Pt and/or Pd complex which has phosphine ligands and/or phosphite ligands as catalyst.

It has been found that 2-alkynoic esters can be prepared directly under very mild conditions and with very high yields from terminal alkynes and chloroformates using a palladium catalyst, preferably in the presence of a stoichiometric amount of base.

The catalysts employed for this purpose are Pt and Pd complexes, preferably Pd complexes, which have phosphine ligands and/or phosphite ligands. A large number of ligands are suitable as phosphine ligands or phosphite ligands. For example, the ligands may have the general formula PXYZ where X, Y and Z independently are alkyl, aryl, alkoxy or aryloxy radicals having up to 18 C atoms. Alkyl or aryl radicals are preferred, in particular aryl radicals. Corresponding ligands are described, for example, in DE-A-1 593 277. The Pd complexes are preferably Pd(0) and/or Pd(II) complexes having organic phosphine or phosphite ligands, in particular triarylphosphine ligands in which the aryl radicals can independently be substituted by $C_{1-6}$-alkyl radicals, preferably linear $C_{1-4}$-alkyl radicals, in particular linear $C_{1-3}$-alkyl radicals. The catalysts may moreover be formed in situ during the reaction. Examples of Pd(0) complexes are tetrakis(triphenyl-phosphine)palladium(0) ($Pd(PPh_3)_4$) and tris(di-benzylideneacetone)dipalladium(0) in the presence of tri-o-tolylphosphine. The complexes can be composed, for example, of monodentate or bidentate ligands. Examples of suitable complex structures are the following:

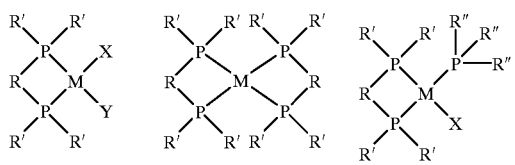

where the meanings are
M Pd, Pt, preferably Pd
R independently at each position organic radicals which can be bonded to the phosphorus atoms via O and/or C atoms, in particular aryl radicals or aryloxy radicals with 2 sites capable of bonding,
R', R" independently at each position monovalent organic radicals, in particular aryl and/or aryloxy radicals
X, Y independently monovalent anionic ligands.

The charges are equalized, where appropriate by means of cations or anions not involved in coordinate bonds.

It is preferred for the monovalent radicals to be derived from benzene or phenol and for the divalent radicals to be derived from biphenyl, 1,1'-binaphthyl, biphenyloxy radicals and/or 1,1'-binaphthyloxy radicals. All the aromatic radicals can be substituted, for example by one or more $C_{1-6}$-alkyl radicals or corresponding alkoxy radicals. The biphenyl and binaphthyl radicals, and radicals derived therefrom, are bonded to the phosphorus atom by 2 positions in the molecule. The two positions may be bonded to the same phosphorus atom. It is also possible for them to be bonded to different phosphorus atoms and result in bridged structures which have, for example, 2 phosphorus atoms and 3 of said radicals. Corresponding suitable bidentate phosphite ligands are described in U.S. Pat. No. 5,512,695. The phosphite ligands described therein can also be employed in analogous form as phosphine ligands. Further suitable monodentate and bidentate aromatic ligands are described in WO 95/29153. The described ligands may likewise be employed as phosphine or phosphite ligands. Examples of Pd(II) complexes which can be used are those with monodentate or bidentate phosphine ligands such as $Pd(PPh_3)_2Cl_2$ and $Pd(Ph_2P(CH_2)_2PPh_2)Cl_2$, which are employed where appropriate in the presence of additional phosphine ligands. Another example of a Pd(II) complex is a mixture of Pd(II) acetate and triphenylphosphine. The amount of Pd catalyst employed is generally from 0.01 to 10% by weight, preferably 0.5–3% by weight, in particular 1 to 2% by weight, based on the amount of alkyne employed. They are preferably present in the reaction mixture in homogeneous phase. The above statements apply to Pt complexes correspondingly.

The reaction temperature is generally from 0 to 120° C., preferably 20 to 80° C., particularly preferably 30 to 50° C., in particular about 40° C.

The reaction can be carried out without solvent or in the presence of an inert solvent such as dichloromethane. The reaction can be carried out under atmospheric pressure or elevated pressure, preferably a pressure of from 1 to 20 bar (absolute). After the reaction is complete, the product can be isolated in pure form by distillation.

The process according to the invention can be carried out continuously or batchwise.

Chloroformates of the general formula (II)

$$R^1-O-CO-Cl \quad (II)$$

are employed in the process according to the invention. In this case, $R^1$ is a $C_{1-16}$-, preferably $C_{1-6}$-, in particular $C_{1-4}$-alkyl, $C_{6-12}$-aryl, preferably phenyl, $C_{7-12}$-aralkyl, preferably $C_{7-12}$-phenylalkyl or $C_{7-12}$-alkylaryl, preferably $C_{7-12}$-alkylphenyl radical. $R^1$ as alkyl radical can be linear or branched. $R^1$ is preferably an unbranched alkyl radical.

The chloroformate of the general formula (II) is reacted with an alkyne of the general formula (III)

$$R^2-C\equiv C-H \quad (III).$$

In this case, $R^2$ has the same meaning as described above for $R^1$. The $R^1$ and $R^2$ radicals may, however, be chosen independently of one another. In addition, $R^2$ may also be a hydrogen atom. Particularly preferred $R^2$ radicals are n-butyl, phenyl or hydrogen.

The reaction is preferably carried out in the presence of at least one base. A stoichiometric amount of at least one sterically hindered amine is preferably employed for this. The sterically hindered amines have sterically demanding substitution either on the nitrogen atom or on the organic radical. Examples are amines with sterically demanding substitution which are derived from piperidine or pyridine. Suitable substituents in the piperidine and pyridine structures are $C_{1-16}$-, preferably $C_{1-4}$-, in particular $C_{1-2}$-alkyl radicals, specifically methyl radicals. Piperidine may, for example, be substituted by 1 to 7 methyl groups, preferably 3 to 5 methyl groups. Pyridine may likewise be substituted by methyl groups, in which case the pyridine preferably has at least one $C_{1-6}$-alkylamino substituent. It is preferably located in position 4. Examples of suitable bases are 1,2,2,6,6-pentamethylpiperidine and 4-dimethylaminopyridine, which are preferably employed as mixtures. In this case, the molar ratio of 1,2,2,6,6-pentamethylpiperidine to 4-dimethylaminopyridine is preferably 0.5:1 to 1:0.5, particularly preferably 0.8:1 to 1:0.8, in particular 0.9:1 to 1:0.9.

The invention is explained in detail below by means of examples.

EXAMPLE 1

3.25 g (2.75 mmol) of tetrakis(triphenylphosphine) palladium(0) are introduced into 250 ml of dichloromethane in a 500 ml round-bottomed flask under argon. The dark brown solution is stirred at room temperature for 1 h. Then 150 mg (1.25 mmol) of 4-dimethylaminopyridine, 21.5 g (137.5 mmol) of 1,2,2,6,6-pentamethylpiperidine and 10.25 g (125 mmol) of 1-hexyne are added and heated to reflux at 40° C. Subsequently, 17 g (125 mmol) of n-butyl chloroformate are added dropwise over the course of 60 min. After a reaction time of 24 h, the reaction mixture is worked up by distillation to isolate n-butyl 2-heptynoate in 90% yield.

EXAMPLE 2

1.26 g (1.375 mmol) of tris(dibenzylideneacetone)-dipalladium(0) and 3.34 g (11 mmol) of tri-o-tolylphosphine are introduced into 125 ml of dichloromethane in a 250 ml round-bottomed flask under argon. The reddish brown solution is stirred at room temperature for 1 h. Then 75 mg (0.625 mmol) of 4-dimethylaminopyridine, 10.75 g (68.75 mmol) of 1,2,2,6,6-pentamethylpiperidine and 6.38 g (62.5 mmol) of phenylacetylene are added. The mixture is heated to reflux at 42° C. and then 8.53 g (62.5 mmol) of n-butyl chloroformate are added dropwise over the course of 30 min. After 20 h, the reaction mixture is worked up by distillation to isolate n-butyl phenyl propynoate in 98% yield.

EXAMPLE 3

0.25 g (1.1 mmol) of palladium(II) acetate and 1.16 g (4.4 mmol) of triphenylphosphine are introduced into 100 ml of dichloromethane in a 250 ml round-bottomed flask under argon. The yellow solution is stirred at room temperature for 1 h. Then 0.06 g (0.5 mmol) of 4-dimethylaminopyridine, 8.53 g (55.5 mmol) of 1,2,2,6,6-pentamethylpiperidine and 5.1 g (50 mmol) of phenylacetylene are added. The mixture is heated to reflux at 40° C. and then 6.83 g (50 mmol) of n-butyl chloroformate are added dropwise over the course of 1 h. After a reaction time of 20 h, the reaction mixture is worked up by distillation to isolate n-butyl phenylpropynoate in 85% yield.

EXAMPLE 4

0.42 g (0.36 mmol) of tetrakis(triphenylphosphine) palladium(0), 20 mg (0.16 mmol) of 4-dimethylaminopyridine and 2.87 g (18.5 mmol) of 1,2,2,6,6-pentamethylpiperidine are introduced into 30 ml of dichloromethane in a 60 ml autoclave under argon. Then 10 bar of acetylene are injected, and the autoclave is heated to 40° C. 5 g (36.6 mmol) of n-butyl chloroformate are pumped in over the course of 10 min, and then acetylene is further injected to 20 bar. The amount of acetylene taken up is replenished hourly over the course of 24 h, and, after cooling, the reaction discharge is flushed with nitrogen and the reaction mixture is distilled. n-Butyl propiolate is isolated in 85% yield.

We claim:

1. A process for preparing 2-alkynoic esters of the general formula (I), $$R^1-O-CO-C-C-R^2 \quad (I)$$

in which $R^1$ and $R^2$ independently are $C_{1-12}$-alkyl, $C_{6-12}$-aryl, $C_{7-12}$-aralkyl or $C_{7-12}$ and $R^2$ can also be hydrogen, by reacting a chloroformate of the general formula (II), $$R^1-O-CO-Cl \quad (II)$$

in which $R^1$ has the above meaning, with an alkylne of the general formula (III), $$R^2-C-C-H \quad (III)$$

in which $R^2$ has the above meaning, in the presence of a Pt and/or Pd complex, which has phosphine ligands and/or phosphite ligands, as catalyst.

2. A process as claimed in claim 1, wherein $R^2$ is hydrogen, a $C_{1-16}$-alkyl or a phenyl radical.

3. A process as claimed in claim 1, wherein $R^1$ is lineaar $C_{1-16}$-alkyl radical.

4. A process as claimed in claim 1, wherein the reaction is carried out in the presence of at least one base.

5. A process as claimed in claim 4, wherein a stoichiometric amount of at least one sterically hindered amine is employed as base.

6. A process as claimed in claim 1, wherein the Pd complex is a Pd(0) and/or Pd(II) complex having organic phosphine or phosphite ligands.

7. A process as claimed in claim 1, wherein the catalyst is formed in situ during the reaction.

8. A process as claimed in claim 1, wherein the catalyst employed is tetrakis(triphenylphosphine)palladium(0).

9. A process as claimed in claim 1, wherein the Pd complex is a Pd(0) and/or Pd(II) complex having triarylphosphine ligands in which the aryl radicals can independently be substituted by Clan alkyl groups.

\* \* \* \* \*

UNITED STATES PATENT AND TRADEMARK OFFICE
CERTIFICATE OF CORRECTION

PATENT NO. : 6,153,786
DATED : November 28, 2000
INVENTOR(S) : Henkelmann et al.

It is certified that error appears in the above-identified patent and that said Letters Patent is hereby corrected as shown below:

Column 4, claim 1,
Line 42, after "$C_{7-12}$" insert -- -alkylaryl --.

Column 4, claim 3,
Line 56, "lineaar" should be -- linear --

Column 6, claim 9,
Last line, "Clan" should be -- $C_1$-$C_6$- --.

Signed and Sealed this

Twenty-fifth Day of September, 2001

Attest:

NICHOLAS P. GODICI
Attesting Officer    Acting Director of the United States Patent and Trademark Office